United States Patent [19]

Hagen et al.

[11] 3,960,862
[45] June 1, 1976

[54] 1,3-DIAZACYCLOALKENO-[1,2,D]-BENZO-[F-]-1,3,4-THIADIAZEPINES

[75] Inventors: Helmut Hagen, Frankenthal; Juergen Niemeyer, Gruenstadt, both of Germany

[73] Assignee: BASF Aktiengesellschaft, Ludwigshafen (Rhine), Germany

[22] Filed: Sept. 23, 1974

[21] Appl. No.: 508,579

[30] Foreign Application Priority Data

Sept. 29, 1973 Germany.......................... 2349064

[52] U.S. Cl....................... 260/256.5 R; 260/309.6; 424/251; 424/273

[51] Int. Cl.$^2$.................................. C07D 239/00
[58] Field of Search................................. 260/256.5

[56] References Cited
UNITED STATES PATENTS 3,842,080 10/1974 Szmuszkovicz............... 260/256.4 F

*Primary Examiner*—Leonard Schenkman
*Attorney, Agent, or Firm*—Johnston, Keil, Thompson & Shurtleff

[57] ABSTRACT

1,3-Diazacycloalkeno-[1,2-d]-benzo-[f]-1,3,4-thiadiazepines and their acid addition salts, a process for their production and their pharmacological use.

6 Claims, 1 Drawing Figure

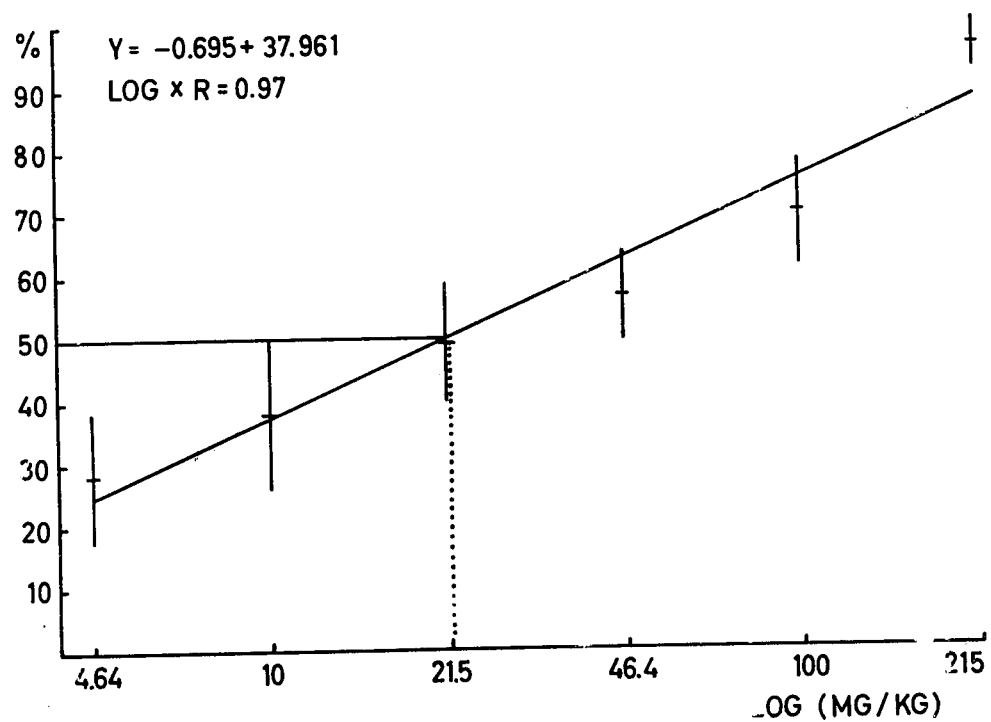

1,3-DIAZACYCLOALKENO-[1,2,D]-BENZO-[F-]-1,3,4-THIADIAZEPINES

The invention relates to 1,3-diazacycloalkeno-[1,2-d]-benzo-[f]-1,3,4-thiadiazepines of the formula (I):

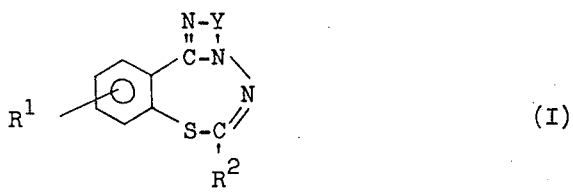

in which $R^1$ is hydrogen, halogen, nitro or linear or branched alkyl;

Y is one of the radicals —$CH_2$—$CH_2$— or —$CH_2$—$CH_2$—$CH_2$— in which on one or more of the carbon atoms a hydrogen atom may be replaced by lower alkyl of one to four carbon atoms and $R^2$ is a mononuclear or polynuclear carbocyclic aromatic radical, a benzoyl radical which may bear substituents or a heterocyclic radical, their acid addition salts, a process for their production and their pharmacological use.

Suitable halogen atoms for $R^1$ are fluorine, chlorine, bromine and iodine and particularly suitable linear or branched alkyl radicals are those of one to seven carbon atoms such as methyl, ethyl, isopropyl, butyl, isobutyl, pentyl, hexyl or heptyl.

In addition to unsubstituted ethylene and propylene radicals, A may be for example an ethylene or propylene radical bearing methyl, ethyl, or isobutyl radicals as substituents such as methylethylene, 1-methylpropylene, 2-isobutylpropylene, 1-methyl-3-ethylpropylene and 1,3-diethylpropylene.

Phenyl and naphthyl are particularly suitable carbocyclic aromatic radicals $R^2$. The aromatic radical or the phenyl ring when $R^2$ is benzoyl may bear one or more and if desired different substituents, such as fluoro, chloro, bromo, iodo, nitro, hydroxy, cyano, alkoxy of one to four carbon atoms such as methoxy, ethoxy, propoxy or isobutoxy, or lower alkyl of one to four carbon atoms such as methyl, ethyl, isopropyl, butyl or isobutyl.

Pyridyl and furyl radicals are particularly suitable as heterocyclic radicals for $R^2$.

The new compounds may be prepared in good yields and high purity by cyclizing in the presence of an acid reagent which eliminates water a 2-[2'-(hydroxyiminoformylthio)-phenyl]-1,3-diazacycloalkene hydrochloride of the general formula (II)

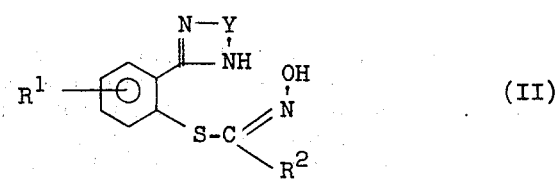

in which $R^1$, Y and $R^2$ have the above meanings.

This reaction may be represented for example for 2-[2'-($\alpha$-hydroxyiminobenzylthio)-phenyl]-$\Delta^2$-imidazoline hydrochloride by the following equation:

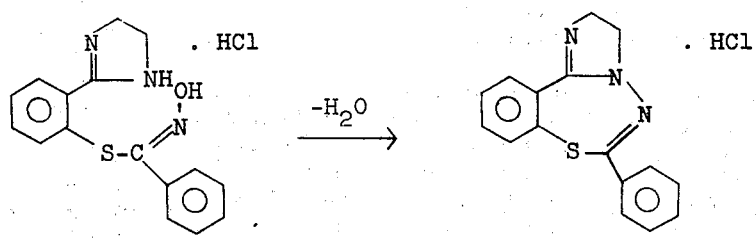

The compounds of formula (II) may easily be obtained by reacting a benzothietane-2-spiro-2'-(1',3'-diazacycloalkane) of the general formula (III) whose structure may also be represented in a second form (formula (IIIa)):

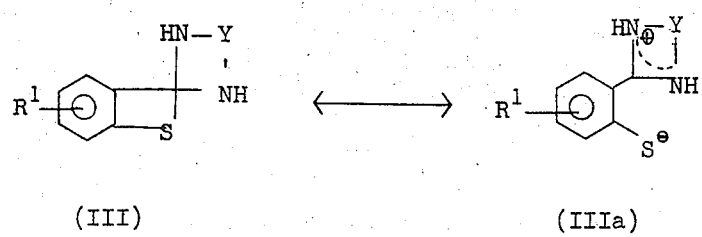

in which $R^1$ and Y have the above meanings with a hydroxamic acid chloride of the formula (IV):

(IV)

in which R² has the said meanings and if desired liberating the base from the acid adduct obtained.

The reaction may be represented for benzothietane-2-spiro-2'-imidazolidine and benzhydroxamic acid chloride by the following equation:

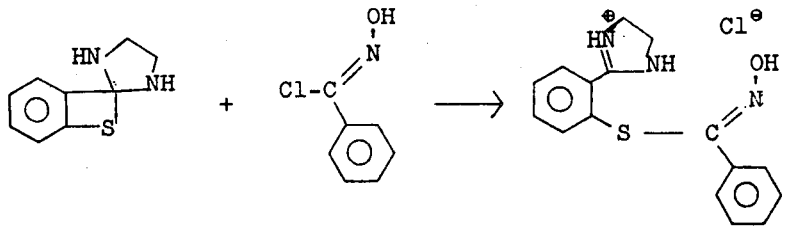

Compounds of the formula (III) may be prepared for example according to the method described in German Laid-Open Patent Specification No. P 20,34,987.5 by the reaction of a halobenzaldehyde compound with a diaminoalkane and sulfur. Methods for the production of hydroxamic acid chlorides of the formula (IV) for example by the chlorination of substituted benzaldoximes are described in Houben-Weyl, "Methoden der organischen Chemie", 4th edition, volume VIII, pages 691 et seq.

Compounds (III) and (IV) are conveniently reacted with one another in stoichiometric proportions. The compound of formula (IV) may however conveniently be used in excess, for example up to an excess of 1.2 times the stoichiometric amount based on compound (IV).

The reactions are carried out as a rule at a temperature of from 10° to 140°C and preferably from 20° to 60°C. It is convenient to use for the reaction an inert organic solvent, for example an aromatic hydrocarbon such as benzene or toluene, a lower alcohol such as methanol, ethanol, a propanol or butanol, a glycol ether such as glycol monomethyl ether or glycol monoethyl ether, or mixtures of these solvents. The starting compounds are preferably completely dissolved in the solvent or solvent mixture.

The reaction may be carried out at atmospheric pressure or if desired at superatmospheric pressure. Batchwise or continuous operation is possible.

The reaction may be carried out as follows: A solution of compound (III) and compound (IV) in the same solvent or different solvents are brought together and then stirred for from 2 to 8 hours at the preferred reaction temperature of from 20° to 60°C. The reaction product which is deposited in crystalline form if necessary after concentration of the reaction solution is separated by filtration and if necessary purified by recrystallization.

It should be mentioned that in the compounds of formula (III) the double bond to the positively charged nitrogen atom does not need to be fixed as represented in formula (IIIa).

For the production of the compounds according to the invention the starting materials of formula (II) are if desired dissolved or suspended in an inert organic solvent, preferably an aromatic hydrocarbon such as benzene, toluene or xylene. Cyclization of compound (II) into the benzothiadiazepines of formula (I) is conveniently carried out at a temperature of from 10° to 150°C and preferably from 25° to 80°C, in the presence of an acid reagent which eliminates water such as thionyl chloride, phosphorus oxychloride, phosphorus pentachloride or polyphosphoric acid. The agent for eliminating water may also itself be the solvent and thionyl chloride and phosphorus oxychloride are particularly suitable in this respect.

Basic water-eliminating agents or purely thermal methods are far less suitable than the conditions according to the invention for the cyclization of the starting materials (II).

The reaction may conveniently be carried out as follows: The water-eliminating agent, for example thionyl chloride, is added in portions to a solution or suspension of the starting compound (II) in the inert organic solvent used, for example benzene. The reaction is slightly exothermic in some cases; as a rule the mixture is heated for several hours at the boiling point of the solvent used until complete conversion has taken place. The insoluble benzothiadiazepine hydrochloride is isolated by decantation or suction filtration and conveniently recrystallized from methanol or ethanol.

Since the chlorides of compound (II) are the preferred starting compounds, the hydrochlorides of the compounds according to the invention are preferably prepared. Obviously anion-exchange reactions, double decompositions and the like may be used to prepare the salts of a great variety of acids. The anions of inorganic or organic non-toxic pharmacologically compatible acids are preferred. Examples of suitable acids are hydrobromic acid, sulfuric acid, acetic acid, oxalic acid, maleic acid, succinic acid, glutaric acid, tartaric acid and citric acid.

The free benzothiadiazepines (I) are easily obtained from the hydrochlorides for example by conventional methods; the free compounds may then be converted into salts by reaction with appropriate acids.

The following benzothiadiazepines are given as examples according to the invention: imidazolinobenzothiadiazepines which bear a substituent for R¹ on the benzene ring:

imidazolino-[1,2-d]-7-chlorobenzo-[f]-2-phenyl-1,3,4-thiadiazepine and the corresponding 2-(2-chlorophenyl), 2-(4-chlorophenyl), 2-(3-nitrophenyl),
2-(2-nitro-6-chlorophenyl), 2-(4-bromophenyl),
2-(4-isopropylphenyl), 2-(4-hydroxyphenyl),
2-(4-methoxyphenyl), 2-(2-pyridyl) and 2-benzoyl compounds of imidazolino-[1,2-d]-7-bromobenzo-[f]-2-phenyl-1,3,4-thiadiazepine, imidazolino-[1,2-d]-7-nitrobenzo-[f]-2-phenyl-1,3,4-thiadiazepine, imidazolino-[1,2-d]-7-methylbenzo-f]-2-phenyl-1,3,4-thiadiazepine and the corresponding 4-(5)-methylimidazolino compounds;

Tetrahydropyrimidinobenzothiadiazepines which bear a substituent for $R^1$ on the benzene ring:

tetrahydropyrimidino-[1,2-*d*]-7-chlorobenzo-[*f*]-2-phenyl-1,3,4-thiadiazepine and the corresponding 2-(2-chlorophenyl), 2-(4-chlorophenyl), 2-(3-nitrophenyl)-, 2-(2-nitro-6-chlorophenyl), 2-(4-bromophenyl), 2-(4-ethylphenyl), 2-(2,4-dihydroxyphenyl), 2-(4-methoxyphenyl), 2-(2-furyl) or 2-benzoyl compound or tetrahydropyrimidino-[1,2-*d*]-7-bromobenzo-[*f*]-2-phenyl-1,3,4-thiadiazepine, tetrahydropyrimidino-[1,2-*d*]-7-nitrobenzo-[*f*]-2-phenyl-1,3,4-thiadiazepine, tetrahydropyrimidino-[1,2-*d*]-7-methylbenzo-[*f*]-2-phenyl-1,3,4-thiadiazepine and the corresponding 4,6-diethyltetrahydropyrimidino compounds.

The compounds which can be prepared by the process of the invention have valuable pharmacological properties. In pharmacological screening for example increase in blood pressure, sympathomimetric effects and effects on the central nervous system are shown. Other compounds are capable of neutralizing eyelid paralysis by tetrabenazine; others have excellent analgesic, spasmolytic, anti-inflammatory or broncholytic properties.

The compounds of Example 4 and 18 may be singled out for their pharmacological effect, particularly their analgesic properties.

The analgesic effect of tetrahydropyrimidino-[1,2-*d*]-benzo-[*f*]-2-(3-nitrophenyl)-1,3,4-thiadiazepine (Example 18) is demonstrated in the writhing test on mice.

In this test p-benzoquinone (phenylquinone) in a 0.02% aqueous solution in a volume of 10 ml/kg of body weight i.p. serves to initiate pain. The typical writhing reactions which occur after a certain latency period are recorded in their frequency; decrease in the writhing frequency is evaluated as analgesic effect. The following Table indicates the numerical connection between dosage and effect after peroral application of the active ingredient.

TABLE

| Dosage mg/kg | n | $-\Sigma R-$ $x \pm sx$ | $P^a$ | % effect (Decrease in the writhing reactions) |
|---|---|---|---|---|
| 0 | 60 | 20.5 ± 0.88 | — | — |
| 4.64 | 10 | 14.7 ± 2.1 | <0.02 | 28.1 ± 10.3 |
| 10 | 10 | 12.7 ± 2.4 | <0.002 | 37.9 ± 11.8 |
| 21.5 | 10 | 10.4 ± 1.9 | <0.001 | 49.1 ± 9.4 |
| 46.4 | 10 | 8.9 ± 1.5 | <0.001 | 56.5 ± 7.2 |
| 100 | 10 | 6.2 ± 1.7 | <0.001 | 69.7 ± 8.4 |
| 215 | 10 | 0.8 ± 0.8 | <0.001 | 96.1 ± 3.9 |

$^a$T-test for independent random samples, bilateral questioning, significant down to 0.05, below 0.001 not given. n = number of test animals. The values are mean values ± mean error of the mean value.

The same interrelation is shown in the drawing wherein the graphical chart plots the dosage as log (MG/KG) against the % effect.

According to the regression line there is an $ED_{50}$ of 21.6 mg/kg after peroral application. The behavior of animals treated with the compound is consistent with a central nervous system depressant action. The inhibition in percent is plotted as ordinates and the dosage is plotted logarithmically as abscissae. The effective dose is much below the range of toxic doses.

Preparations which contain the new compounds as active ingredients may be prepared by any expert by conventional methods appropriate to the desired use. Pharmaceutically acceptable excipients such as the conventional diluents and carriers, may be employed in formulating the preparations.

The following Examples illustrate the invention; parts referred to are by weight; the compounds specified have been checked by elementary analysis.

EXAMPLE 1

Imidazolino-[1,2-*d*]-benzo-[*f*]-2-phenyl-1,3,4-thiadiazepine:

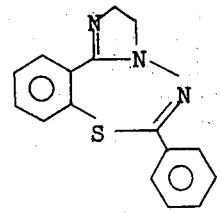

100 parts of thionyl chloride is added at 25°C within 10 minutes to a suspension of 33.4 parts of 2-[2'-(α-hydroxyiminobenzylthio)-phenyl]-Δ²-imidazoline hydrochloride in 500 parts of benzene. The reaction mixture is stirred for three hours at 25°C. The insoluble crude product which initially is oily is separated by decantation and after having been ground with ether is filtered off and recrystallized from ethanol.

The yield is 30 parts (95% of theory). Melting points: hydrochloride 256° to 258°C; free base 188° to 190°C; hydrogen sulfate 214°C.

EXAMPLE 2

Imidazolino-[1,2-*d*]-benzo-[*f*]-2-(2-chlorophenyl)-1,3,4-thiadiazepine:

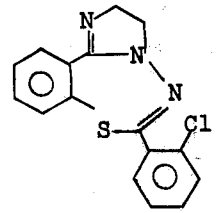

100 parts of thionyl chloride is added within 10 minutes at 25°C to a suspension of 37 parts of 2-[2'-(α-hydroxyimino-2''-chlorobenzylthio)-phenyl]-Δ²-imidazoline hydrochloride in 500 parts of benzene. The reaction mixture is heated at refluxing temperature for 10 hours. After the whole has cooled the insoluble crude product is suction filtered, washed with benzene and recrystallized from ethanol.

The yield is 26 parts (74% of theory). Melting points: hydrochloride 278° to 283°C; free base 173° to 175°C; hydrogen sulfate 233°C.

EXAMPLE 3

Imidazolino-[1,2-*d*]-benzo-[*f*]-2-(4-chlorophenyl)-1,3,4-thiadiazepine:

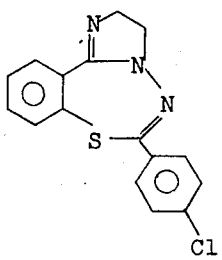

200 parts of thionyl chloride is added at 25°C within 10 minutes to a suspension of 74 parts of 2-[2'-(α-hydroxyimino-4''-chlorobenzylthio)-phenyl]-Δ²-imidazoline hydrochloride in 900 parts of benzene. The reaction mixture is stirred for 12 hours at 25°C. The insoluble crude product is suction filtered, washed with benzene and recrystallized from ethanol.

The yield is 57 parts (81% of theory). Melting points: hydrochloride 258° to 263°C; free base 148°C; hydrogen sulfate 253°C.

EXAMPLE 4

Imidazolino-[1,2-d]-benzo-[f]-2-(3-nitrophenyl)-1,3,4-thiadiazepine:

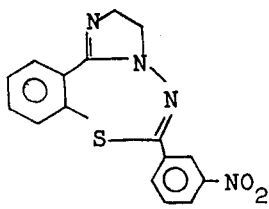

100 parts of thionyl chloride is added within 10 minutes at 25°C to a suspension of 38 parts of 2-[2'-(α-hydroxyimino-3''-nitrobenzylthio)-phenyl]-Δ²-imidazoline hydrochloride in 300 parts of benzene. The reaction mixture is heated for six hours at refluxing temperature and then worked up as described in Example 2.

The yield is 30 parts (83% of theory). Melting points: hydrochloride 278° to 280°C; free base 189° to 191°C; hydrogen sulfate 207° to 209°C.

EXAMPLE 5

Imidazolino-[1,2-d]-benzo-[f]-2-(2-nitro-6-chlorophenyl)-1,3,4-thiadiazepine:

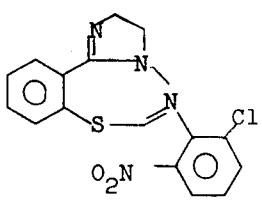

100 parts of thionyl chloride is added within 5 minutes at 25°C to a suspension of 41.3 parts of 2-[2'-(α-hydroxyimino-2''-nitro-6''-chlorobenzothio)-phenyl]-Δ²-imidazoline hydrochloride in 300 parts of benzene. The reaction mixture is heated for 3 hours at refluxing temperature and then worked up as described in Example 2.

The yield is 26 parts (66% of theory). Melting points: hydrochloride 270° to 273°C; free base 243° to 245°C; hydrogen sulfate 249° to 251°C.

EXAMPLE 6

Imidazolino-[1,2-d]-benzo-[f]-2-benzoyl-1,3,4-thiadiazepine:

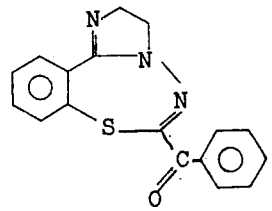

300 parts of thionyl chloride is added within 10 minutes at 25°C to a suspension of 72.4 parts of 2-[2'-(benzoylhydroxyiminoformylthio)-phenyl]-Δ²-imidazoline hydrochloride in 800 parts of benzene. The reaction mixture is heated for 5 hours at reflux temperature and then worked up as described in Example 2.

The yield is 35 parts (51% of theory). Melting points: hydrochloride 288° to 290°C; free base 194°C.

EXAMPLE 7

Imidazolino-[1,2-d]-7-chlorobenzo-[f]-2-phenyl-1,2,3-thiadiazepine:

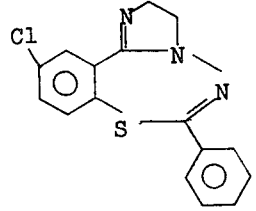

250 parts of thionyl chloride is added at 25°C within 10 minutes to a suspension of 37 parts of 2-[2'-(α-hydroxyiminobenzylthio)-5'-chlorophenyl]-Δ²-imidazoline hydrochloride in 500 parts of benzene. The reaction mixture is heated for 3 hours at refluxing temperature and then worked up as described in Example 2.

The yield is 33 parts (94% of theory). Melting points: hydrochloride 297° to 300°C; free base 176° to 178°C; hydrogen sulfate 247° to 250°C.

EXAMPLE 8

Imidazolino-[1,2-d]-7-chlorobenzo-[f]-2-(2-chlorophenyl)-1,3,4-thiadiazepine:

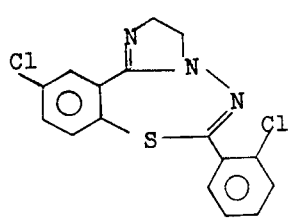

250 parts of thionyl chloride is added at 25°C within 10 minutes to a suspension of 40.3 parts of 2-[2'-(α-hydroxyimino-2''-chlorobenzylthio)-phenyl]-Δ²-imidazoline hydrochloride in 500 parts of benzene. The reaction mixture is heated for 3 hours at refluxing temperature and then worked up as described in Example 2.

The yield is 35 parts (91% of theory). Melting points: hydrochloride 283° to 285°C; free base 211° to 213°C; hydrogen sulfate 276° to 278°C.

EXAMPLE 9

Imidazolino-[1,2-*d*]-7-chlorobenzo-[*f*]-2-(4-chlorophenyl)-1,3,4-thiadiazepine:

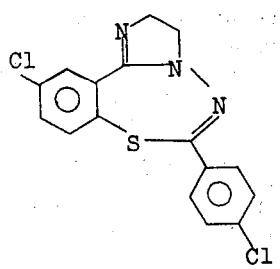

330 parts of thionyl chloride is added within 10 minutes at 25°C to a suspension of 80.5 parts of 2-[2'-(α-hydroxyimino-4''-chlorobenzylthio)-phenyl]-Δ²-imidazoline hydrochloride in 1000 parts of benzene. The reaction mixture is heated for 5 hours at refluxing temperature and then worked up as described in Example 2.

The yield is 66 parts (86% of theory); melting points: hydrochloride 301° to 305°C; free base 206° to 207°C; hydrogen sulfate 231° to 232°C.

EXAMPLE 10

4-(5)-methylimidazolino-[1,2-*d*]-benzo-[*f*]-2-phenyl-1,3,4-thiadiazepine:

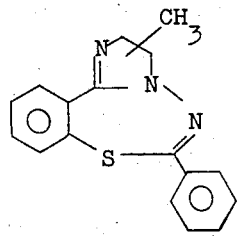

66 parts of thionyl chloride is added within 5 minutes at 25°C to a suspension of 33 parts of 2-[2'-(α-hydroxyiminobenzylthio)-phenyl]-4-methyl-Δ²-imidazoline hydrochloride in 300 parts of benzene. The reaction mixture is stirred for 12 hours at 25°C and then worked up as described in Example 2.

The yield is 26.5 parts (85% of theory). Melting points: hydrochloride 264° to 269°C; free base 160° to 162°C; hydrogen sulfate 164° to 168°C.

EXAMPLE 11

4-(5)-methylimidazolino-[1,2-*d*]-benzo-[*f*]-2-(2-chlorophenyl)-1,3,4-thiadiazepine:

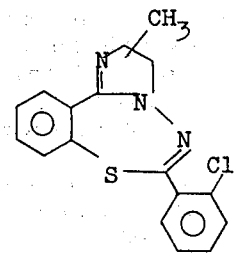

125 parts of thionyl chloride is added within 10 minutes at 25°C to a suspension of 38.2 parts of 2-[2'-(α-hydroxyimino-2''-chlorobenzylthio)-phenyl]-4-methyl-Δ²-imidazoline hydrochloride in 400 parts of benzene. The reaction mixture is heated for 30 minutes at refluxing temperature. The clear solution formed is evaporated to dryness and the residue is recrystallized from ethanol.

The yield is 22 parts (60% of theory). Melting points: hydrochloride 262° to 264°C; free base 167° to 170°C; hydrogen sulfate 206° to 208°C.

EXAMPLE 12

4-(5)-methylimidazolino-[1,2-*d*]-benzo-[*f*]-2-(4-chlorophenyl)-1,3,4-thiadiazepine:

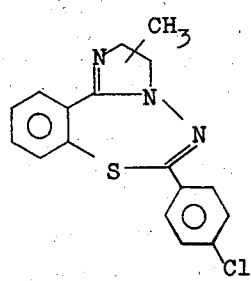

150 parts of thionyl chloride are added within 10 minutes at 25°C to a suspension of 38.2 parts of 2-[2'-(α-hydroxyimino-4''-chlorobenzylthio)-phenyl]-4-methyl-Δ²-imidazoline hydrochloride in 400 parts of benzene. The reaction mixture is stirred for 12 hours at 25°C and then worked up as described in Example 1.

The yield is 29 parts (80% of theory). Melting points: hydrochloride 246° to 258°C; free base 134° to 135°C; hydrogen sulfate 193° to 196°C.

EXAMPLE 13

4-(5)-methylimidazolino-[1,2-*d*]-benzo-[*f*]-2-(3-nitrophenyl)-1,3,4-thiadiazepine:

400 parts of thionyl chloride is added within 15 minutes at 25°C to a suspension of 100 parts of 2-[2'-(α-hydroxyimino-3''-nitrobenzylthio)-phenyl]-4-methyl-Δ²-imidazoline hydrochloride in 800 parts of benzene. The reaction mixture is heated for 4 hours at refluxing temperature and then worked up as described in Example 2.

The yield is 60 parts (63% of theory). Melting points: hydrochloride 281° to 283°C; free base 172° to 173°C; hydrogen sulfate 211° to 214°C.

EXAMPLE 14

4-(5)-methylimidazolino-[1,2-d]-benzo-[f]-2-(2-nitro-6-chlorophenyl)-1,3,4-thiadiazepine:

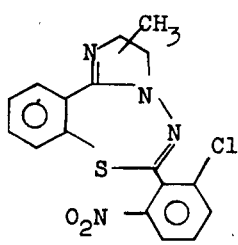

400 parts of thionyl chloride is added within 15 minutes at 25°C to a suspension of 107 parts of 2-[2'-(α-hydroxyimino-2''-nitro-6''-chlorobenzylthio)-phenyl]-4-methyl-Δ²-imidazoline hydrochloride in 800 parts of benzene. The reaction mixture is heated for 3 hours at refluxing temperature and then worked up as described in Example 2.

The yield is 56 parts (55% of theory). Melting points: hydrochloride 256° to 257°C; free base 206° to 208°C; hydrogen sulfate 259° to 261°C.

EXAMPLE 15

Tetrahydropyrimidino-[1,2-d]-benzo-[f]-2-phenyl-1,3,4-thiadiazepine:

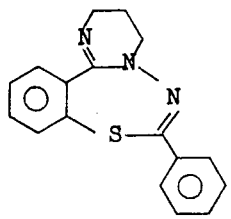

400 parts of thionyl chloride is added within 10 minutes at 25°C to a suspension of 80 parts of 2-[2'-(α-hydroxyiminobenzylthio)-phenyl]-Δ²-tetrahydropyrimidine hydrochloride in 800 parts of benzene. The reaction mixture is heated for 7 hours at refluxing temperature and then worked up as described in Example 2.

The yield is 53 parts (70% of theory). Melting points: hydrochloride 277° to 279°C; free base 156° to 158°C; hydrogen sulfate 180° to 183°C.

EXAMPLE 16

Tetrahydropyrimidino-1,2-d]-benzo-[f]-2-(2-chlorophenyl)-1,3,4-thiadiazepine:

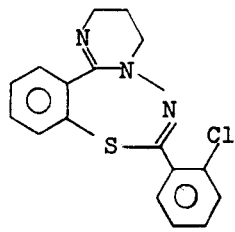

300 parts of thionyl chloride is added within 10 minutes at 25°C to a suspension of 76.5 parts of 2-[2'-(α-hydroxyimino-2''-chlorobenzylthio)-phenyl]-Δ²-tetrahydropyrimidine hydrochloride in 600 parts of benzene. The reaction mixture is heated for 11 hours at refluxing temperature and is then worked up as described in Example 2.

The yield is 56 parts (75% of theory). Melting points: hydrochloride 283° to 285°C; free base 155° to 157°C; hydrogen sulfate 215° to 217°C.

EXAMPLE 17

Tetrahydropyrimidino-[1,2-d]-benzo-[f]-2-(4-chlorophenyl)-1,3,4-thiadiazepine:

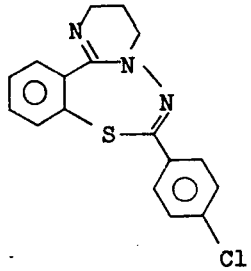

150 parts of thionyl chloride is added within 10 minutes at 25°C to a suspension of 38.3 parts of 2-[2'-(α-hydroxyimino-4''-chlorobenzylthio)-phenyl]-Δ²-tetrahydropyrimidine hydrochloride in 400 parts of benzene. The reaction mixture is heated for 6 hours at refluxing temperature and then worked up as described in Example 2.

The yield is 28 parts (77% of theory). Melting points: hydrochloride 286° to 288°C; free base 175° to 177°C; hydrogen sulfate 194° to 197°C.

EXAMPLE 18

Tetrahydropyrimidino-[1,2-d]-benzo-[f]-2-(3-nitrophenyl)-1,3,4-thiadiazepine:

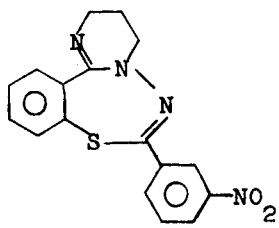

200 parts of thionyl chloride is added within 10 minutes at 25°C to a suspension of 39.3 parts of 2-[2'-(α-hydroxyimino-3''-nitrobenzylthio)-phenyl]-Δ²-tetrahydropyrimidine hydrochloride in 400 parts of benzene. The reaction mixture is heated for 5 hours at refluxing temperature and then worked up as described in Example 2.

The yield is 35 parts (93% of theory). Melting points: hydrochloride 283° to 285°C; free base 142° to 144°C; hydrogen sulfate 230° to 233°C.

EXAMPLE 19

Tetrahydropyrimidino-[1,2-d]-benzo-[f]-2-(2-nitro-6-chlorophenyl)-1,3,4-thiadiazepine:

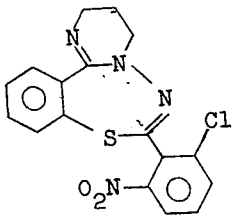

200 parts of thionyl chloride is added at 25°C within 10 minutes to a suspension of 42.7 parts of 2-[2'-(α-hydroxyimino-2''-nitro-6''-chlorobenzylthio)-phenyl]-Δ$^2$-tetrahydropyrimidine hydrochloride in 400 parts of benzene. The reaction mixture is heated for 5 hours at refluxing temperature and then worked up as described in Example 2.

The yield is 25 parts (61% of theory). Melting points: hydrochloride 287° to 290°C; free base 160° to 162°C; hydrogen sulfate 190° to 193°C.

We claim:
1. A compound of the formula (I)

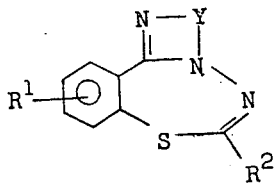

in which:
R$^1$ is hydrogen, halogen, nitro or alkyl of 1 to 7 carbon atoms;
Y is —CH$_2$—CH$_2$—CH$_2$— in which a hydrogen atom on one or more of the carbon atoms may be replaced by lower alkyl of one to four carbon atoms; and
R$^2$ is phenyl or benzoyl in which the benzene ring may be substituted by 1 to 2 substituents selected from the group consisting of fluorine, chlorine, bromine, iodine, nitro, hydroxy, cyano, alkoxy of 1 to 4 carbon atoms and alkyl of 1 to 4 carbon atoms, or an acid addition salt of said compound.

2. A compound as claimed in claim 1 in which R$^1$ is hydrogen, fluorine, chlorine, bromine, iodine, nitro or alkyl of 1 to 7 carbon atoms, Y is —CH$_2$—CH$_2$—CH$_2$—, and R$^2$ is phenyl or benzoyl in which the benzene ring may be substituted by fluorine, chlorine, bromine, iodine, nitro, hydroxy, cyano, or alkoxy or alkyl of 1 to 4 carbon atoms.

3. A compound as claimed in claim 1 in which R$^1$ is hydrogen, methyl, chlorine, bromine or nitro, Y is —CH$_2$—CH$_2$—CH$_2$— in which a hydrogen atom on one or two of the carbon atoms may be replaced by methyl or ethyl, and R$^2$ is phenyl, chlorophenyl, nitrophenyl, nitrochlorophenyl, bromophenyl, ethylphenyl, isopropylphenyl, hydroxyphenyl, methoxyphenyl or benzoyl.

4. A compound as claimed in claim 1 in the form of an acid addition salt of a pharmacologically compatible acid.

5. A compound as claimed in claim 1 in the form of an acid addition salt of hydrochloric acid, hydrobromic acid, sulfuric acid, acetic acid, oxalic acid, maleic acid, succinic acid, glutaric acid, tartaric acid or citric acid.

6. Tetrahydropyrimidino-[1,2-d]-benzo-[f]-2-(3-nitrophenyl)-1,3,4-thiadiazepine.

* * * * *